(12) United States Patent
Lynn et al.

(10) Patent No.: US 10,247,742 B1
(45) Date of Patent: *Apr. 2, 2019

(54) COMPOSITIONS AND METHODS FOR DETECTION OF TARGET CONSTITUENT IN EXHALED BREATH

(71) Applicant: Hound Labs, Inc., Oakland, CA (US)

(72) Inventors: Michael Scott Lynn, Piedmont, CA (US); Hamilton Roger Tang, Los Altos, CA (US); Kate L. Bechtel, Pleasant Hill, CA (US); Peter A. Holst, Los Altos, CA (US)

(73) Assignee: HOUND LABS, INC., Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/875,195

(22) Filed: Jan. 19, 2018

Related U.S. Application Data

(63) Continuation of application No. 15/217,151, filed on Jul. 22, 2016, now Pat. No. 9,921,234.

(60) Provisional application No. 62/351,858, filed on Jun. 17, 2016.

(51) Int. Cl.
| *A61B 5/097* | (2006.01) |
| *G01N 33/94* | (2006.01) |
| *G01N 33/58* | (2006.01) |

(52) U.S. Cl.
CPC ......... *G01N 33/948* (2013.01); *G01N 33/582* (2013.01)

(58) Field of Classification Search
CPC ...... A61B 5/082; A61B 5/412; G01N 21/658; G01N 33/497; G01J 3/44

USPC .......................................................... 436/93
See application file for complete search history.

(56) References Cited

U.S. PATENT DOCUMENTS

| 3,086,833 | A | 4/1963 | Streck |
| 3,676,072 | A | 7/1972 | Krivis |
| 4,288,344 | A | 9/1981 | Reiss |
| 4,771,005 | A | 9/1988 | Spiro |
| 5,361,771 | A | 11/1994 | Craine et al. |
| 5,922,610 | A | 7/1999 | Alving et al. |
| 6,605,444 | B1 * | 8/2003 | Klein ............... G01N 33/54386 422/400 |
| 8,707,758 | B2 | 4/2014 | Keays |

(Continued)

FOREIGN PATENT DOCUMENTS

| EP | 132313 | 9/1991 |
| EP | 2781917 | 9/2014 |
| WO | 2006/083269 | 8/2006 |

OTHER PUBLICATIONS

U.S. Appl. No. 14/997,405, Notice of Allowance dated May 10, 2017.

(Continued)

*Primary Examiner* — Rebecca M Fritchman
(74) *Attorney, Agent, or Firm* — Weaver Austin Villeneuve & Sampson LLP

(57) ABSTRACT

Chemical compositions and methods provide labeling, detection and measurement of target substances in exhaled human breath, and can be implemented in connection with a handheld device—much like a Breathalyzer portable breath testing unit for alcohol—to support rapid quantification of levels of cannabinoid compounds, such as tetrahydrocannabinol (THC), of suspected users at the roadside.

8 Claims, 3 Drawing Sheets

(56) References Cited

U.S. PATENT DOCUMENTS

| | | |
|---|---|---|
| 9,709,581 B1 | 7/2017 | Gordon et al. |
| 9,709,582 B1 | 7/2017 | Gordon et al. |
| 9,726,684 B1 | 8/2017 | Gordon et al. |
| 9,921,234 B1 | 3/2018 | Lynn et al. |
| 9,933,445 B1 | 4/2018 | Lynn et al. |
| 9,945,878 B1 | 4/2018 | Gordon et al. |
| 9,970,950 B1 | 5/2018 | Lynn et al. |
| 2002/0177232 A1 | 11/2002 | Melker et al. |
| 2003/0153844 A1 | 8/2003 | Smith |
| 2004/0043479 A1 | 3/2004 | Briscoe et al. |
| 2005/0105077 A1 | 5/2005 | Padmanabhan et al. |
| 2005/0137491 A1 | 6/2005 | Paz et al. |
| 2007/0077660 A1 | 4/2007 | Glas |
| 2008/0004542 A1* | 1/2008 | Allen .................. A61B 5/411 600/532 |
| 2009/0017555 A1 | 1/2009 | Jehanli et al. |
| 2011/0086364 A1 | 4/2011 | Takkinen et al. |
| 2012/0302907 A1* | 11/2012 | Palmskog ............. A61B 5/082 600/532 |
| 2013/0006068 A1 | 1/2013 | Gemer et al. |
| 2013/0021153 A1 | 1/2013 | Keays |
| 2014/0288454 A1 | 9/2014 | Paz et al. |
| 2014/0366609 A1 | 12/2014 | Beck et al. |
| 2015/0305651 A1 | 10/2015 | Attariwala et al. |

OTHER PUBLICATIONS

U.S. Appl. No. 14/997,405, Office Action dated Jan. 9, 2017.
U.S. Appl. No. 14/997,405, Corrected Notice of Allowability dated Jun. 15, 2017.
U.S. Appl. No. 15/143,379, Office Action dated Oct. 25, 2016.
U.S. Appl. No. 15/143,379, Notice of Allowance dated Mar. 21, 2017.
U.S. Appl. No. 15/143,379, Notice of Allowability dated Jun. 13, 2017.
U.S. Appl. No. 15/143,328, Office Action dated Sep. 1, 2016.
U.S. Appl. No. 15/143,328, Notice of Allowance dated Feb. 10, 2017.
U.S. Appl. No. 15/143,328, Notice of Allowability dated May 18, 2017.
U.S. Appl. No. 15/143,328, Notice of Allowance dated Jun. 14, 2017.
Adams, I.B. et al., "Cannabis: pharmacology and toxicology in animals and humans," Addiction, Nov. 1996;91 (11):1585-614, PubMed abstract 8972919.
Al-Asmari, Ahmed et al., "Method for the quantification of diamorphine and its metabolites in pediatric plasma samples by liquid chromatography-tandem mass spectrometry," Journal of Analytical Toxicology, vol. 34, May 2010.
Atkinson, H.C. et al., "Drugs in human milk. Clinical pharmacokinetic considerations." Clin Pharmacokinet. Apr. 1988;14(4):217-40, PubMed abstract 3292101.
Azorlosa, J.L. et al., "Marijuana smoking: effect of varying delta 9-tetrahydrocannabinol content and number of puffs," J. Pharmacol. Exper. Ther 1992;261:114, abstract.
Bailey, J.R. et al., "Fetal disposition of delta 9-tetrahydrocannabinol (THC) during late pegnancy in the rhesus monkey," Toxicol Appl Pharmacol. Sep. 15, 1987;90(2):315-21, abstract.
Baker, D. et al., "Cannabinoids control spasticity and tremor in a multiple sclerosis model," Nature, Mar. 2, 2000;404(6773):84-7, abstract.
Balabanova, S. et al., "Detection of drugs in sweat," Belt Gerichtl Med. 1990;48:45-9, abstract.
Bashir, W. et al., "Spectrophotometric Determination of Acetone in Acetic Acid", Microchemical Journal, 1983, 28, pp. 77-81.
Beck, Olof et al., "Detection of Delta9-tetrahydrocannabinol in exhaled breath collected from cannabis users," Journal of Analytical Toxicology, vol. 35, Oct. 2011.
Benowitz, Neal L. et al., "Metabolic and psychophysiologic studies of cannabidiol-hexobarbital interaction," Clinical Pharmacology and Therapeutics (1980) 28, 115-120, abstract.
Blanc, Jennifer A. et al., "Adsorption losses from urine-based cannabinoid calibrators during routine use," Clin. Chem. 39/8, 1705-1712 (1993).
Bloom, A.S., Effect of delta9-tetrahydrocannabinol on the synthesis of dopamine and norepinephrine in mouse brain synaptosomes, J Pharmocol Exp Ther. Apr. 1982;221(1):97-103.
Bornheim, Lester M. et al., "Characterization of cytochrome P450 3A inactivation by cannabidiol: possible involvement of cannabidiol-hydroxyquinone as a P450 inactivator," Chem. Res. Toxicol., 1998, 11 (10), pp. 1209-0450.
Bornheim, L.M. et al., "Human hepatic microsomal metabolism of delta 1-tetrahydrocannabinol," Drug Metab Dispos. Mar.-Apr. 1992;20(2):241-6, PubMed abstract 1352216.
Brenneisen, R. et al., "The effect of orally and rectally administered delta 9-tetrahydrocannabinol on spaticity: a pilot study with 2 patients," Int J Clin Pharmocol Ther. Oct. 1996;34(10):446-52.
Brunet, B. et al., "Validation of large white pig as an animal model for the study of cannabinoids metabolism: application to the study of THC distribution in issues," Forensic Sci Int. Sep. 12, 2006;161(2-3):169-74, PubMed abstract 16859848.
Burstein, S. et al., "Isolation and characterization of two major urinary metabolites of 1-tetrahydrocannabinol," Science, Apr. 28, 1972;176(4033):422-3, PubMed abstract 5026162.
Cami, J. et al., "Effect of subject expectancy on the THC intoxication and disposition from smoked hashish cigarettes," Pharmacology Biochemistry and Behavior, vol. 40, Issue 1, Sep. 1991, pp. 115-119.
Challapalli, P.V. et al., "In vitro experiment optimization for measuring tetrahydrocannabinol skin permeation," Int J Pharm. Jul. 25, 2002;241(2):329-39, PubMed abstract 12100860.
Chaturvedi, Arvind K., "Postmortem aviation forensic toxicology: an overview," Journal of Analytical Toxicology, vol. 34, May 2010.
"The Chemistry of Phenols," Zvi Rappoport, editor, © 2003 John Wiley & Sons, Ltd. ISBN: 0-471-49737-1.
Chiang, C. Nora et al., "Prenatal drug exposure: kinetics and dynamics," NIDA Research Monograph 60, 1985.
Christophersen, Asbjorg Solberg et al., "Tetrahydrocannabinol stability in whole blood: plastic versus glass containers," Journal of Analytical Toxicology, vol. 10, Jul./Aug. 1986.
Cirimele, V. et al., "Testing human hair for cannabis. III. Rapid screening procedure for the simultaneous identification of delta9-tetrahydrocannabinol, cannabinol, and cannabidiol," Journal of Analytical Toxicology, vol. 20, Jan./Feb. 1996.
Cone, Edward J. et al., "In vivo adulteration: excess fluid ingestion causes false-negative marijuana and cocaine urine test results," Journal of Analytical Toxicology, vol. 22, Oct. 1998.
Cone, Edward J. et al., "Marijuana-laced brownies: behavioral effects, physiologic effects, and urinalysis in humans following ingestion," Journal of Analytical Toxicology, vol. 12, Jul./Aug. 1988.
Cone, Edward J. et al., "Passive inhalation of marijuana smoke: urinalysis and room air levels of delta-9-tetrahydrocannabinol," Juornal of Analytical Toxicology, vol. 11, May/Jun. 1987.
Crouch, Dennis J. et al., "An evaluation of selected oral fluid point-of-collection drug-testing devices," Journal of Analytical Toxicology, vol. 29, May/Jun. 2005.
Crouch, D.J., "Oral fluid collection: the neglected variable in oral fluid testing," Forensic Sci Int. Jun. 10, 2005;150(2-3):165-73, PubMed abstract 15899565.
Day, David et al., "Detection of THCA in oral fluid by GC-MS-MS," Journal of Analytical Toxicology, vol. 30, Nov./Dec. 2006.
D'Sourza, Deepak Cyril et al., "The psychotomimetic effects of intravenous delta-9-tetrahydrocannabinol in healthy individuals: implications for psychosis," Neuropsychopharmacology (2004) 29, 1558-1572.
Ellis, G.M. Jr. et al., "Excretion patterns of cannabiniod metabolites after last use in a group of chronic users," Clin Pharmacol Ther. Nov. 1985;38(5):572-8, PubMed abstract 3902318.
Ellis, George M. Jr. et al. "Excretion patterns of cannabinoid metabilites after last use," 420 Magazine, Oct. 4, 2011, downloaded from https://www.420magazine.com/forums/drug-testing-urine/153724.

(56) References Cited

OTHER PUBLICATIONS

ElSohly, M. et al., "Potency trends of Delta9-THC and other cannabinoids in confiscated marijuana from 1980-1997," Journal of Forensic Sciences, vol. 45, No. 1, 2000, pp. 24-30.
Feng, Shixia et al., "Simultaneous analysis of Delta9-THC and its major metabolites in urine, plasma, and meconium by GC-MS using an immunoaffinity extraction procedure," Journal of Analytical Toxicology, vol. 24, Sep. 2000.
Fraser, A.D. et al., "Monitoring urinary excretion of cannabinoids by fluorescence-polarization immunoassay: a cannabiniod-to-creatinine ratio study," Ther Drug Monit. Dec. 2002;24(6):746-50, PubMed abstract 12451292.
Fraser, A.D. et al., "Urinary excretion profiles of 11-nor9-carboxy-delta9-tetrahydrocannabinol and 11-hydroxy-delta9-THC: cannabinoid metabolites to creatinine ratio study IV," Forensic Sci Int. Jul. 16, 2004;143(2-3):147-52, PubMed abstract 15240035.
Fraser, A.D. et al., "Urinary excretion profiles of 11-nor-9-carboxy-Delta9-tetrahydrocannabinol. Study III. A Delta9-THC-COOH to creatinine ratio study," Forensic Sci Int. Nov. 26, 2003;137(2-3):196-202, PubMed abstract 14609657.
Garrett, E.R. et al., "Pharmacokinetics of delta9-tetrahydrocannabinol in dogs," J Pharm Sci. Mar. 1977;66(3):395-407, PubMed abstract 845807.
Garrett, Edward R. et al., "Physicochemical properties, solubility, and protein binding of Delta9-tetrahydrocannabinol," J Pharm Sci. Jul. 1974;63(7):1056-64, abstract.
Gjerde, Hallvard et al., "Comparison of drug concentrations in blood and oral fluid collected with the Intercept® sampling device," Journal of Analytical Toxicology, vol. 34, May 2010.
Gjerde, H. et al., "Incidence of alcohol and drugs in fatally injured car drivers in Norway," Accid Anal Prev. Aug. 1993;25(4):479-83, PubMed abstract 8357462.
Goodwin, R.S. et al., "Delta(9)-tetrahydrocannabinol, 11-hydroxy-delta(9)-tetrahydrocannabinol and 11-nor-9-carboxy-delta(9)-tetrahydrocannabinol in human plasma after controlled oral administration of cannabinoids," Ther Drug Monit. Aug. 2006;28(4):545-51, PubMed abstract 16885723.
Green, Mitchell D. et al., "Glucuronidation of opioids, carboxylic acid-containing drugs, and hydroxylated xenobiotics catalyzed by expressed monkey UDP-glucuronosyltransferase 2B9 protein," Drug Metabolism and Disposition, vol. 25, No. 12, (1997).
Gross, Stanley J. et al., "Detection of recent cannabis use by saliva Delta9-THC radioimmunoassay," Journal of Analytical Toxicology, vol. 9, Jan./Feb. 1985.
Grotenhermen, F., "Pharmacokinetics and pharmacodynamics of cannabinids," Clin Pharmacokinet. 2003;42(4):327-60, PubMed abstract 12648025.
Gustafson, Richard A. et al., "Urinary cannabinoid detection times after controlled oral administration of Delta9-tetrahydrocannabinol to humans," Clinical Chemistry 49:7, 1114-1124 (2003).
Gustafson, Richard A. et al., "Urinary pharmacokinetics of 11-Nor-9-carboxy-delta9-tetrahydrocannabinol after controlled oral delat9-tetrahydrocannabinol administration," Journal of Analytical Toxicology, vol. 28, Apr. 2004.
Gustafson, R.A. et al., "Validated method for the simultaneous determination of Delta 9-tetrahydrocannabinol (THC), 11-hydroxy-THC and 11-nor-9-carboxy-THC in human plasma using solid phase extraction and gas chromatography-mass spectrometry with positive chemical ionization," J. Chromatogr B Analyt Technol Biomed Life Sci, Dec. 5, 2003;798(1):145-54, PubMed abstract 14630369.
Guy, G.W. et al., "A phase I, double blind, three-way crossover study to assess the pharmacokinetic profile of cannabis based medicine extract (CBME) administered sublingually in variant cannabinoid ratios in normal healthy male volunteers (GWPK0215)," Journal of Cannabis Therapeutics, vol. 3, No. 4, 2003, pp. 121-152.
Hall, B.J. et al., "Determination of cannabinoids in water and human saliva by solid-phase microextraction and quadrupole ion trap gas chromatography/mass spectrometry," Anal chem. May 1, 1998;70(9):1788-96, PubMed abstract 9599579.

Halldin, M.M. et al., "Identification of in vitro metabolites of delta 1-tetrahydrocannabinol formed by human livers," Drug Metab Dispos. Jul.-Aug. 1982;10(4):297-301, PubMed abstract 6126323.
Hampson, A.J. et al., "Cannabidiol and (−)delta9-tetrahydrocannabinol are neuroprotective antioxidants," Proc Natl Acad Sci U.S.A. Jul. 7, 1998; 95(14): 8268-8273.
Hanson, V.W. et al., "Comparison of 3H- and 125I-radioimmunoassay and gas chromatography/mass spectrometry for the determination of delta9-tetrahydrocannabinol and cannabinoids in blood and serum," Journal of Analytical Toxicology, vol. 7, Mar./Apr. 1983.
Harder, S. et al., "Concentration-effect relationship of delta-9-tetrahydrocannabiol and prediction of psychotropic effects after smoking marijuana," Int J Clin Pharmacol Ther. Apr. 1997;35(4):155-9, PubMed abstract 9112136.
Harvey, D.J. et al., "Metabolites of cannabidiol identified in human urine," Xenobiotic, Mar. 1990;20(3):303-20, PubMed abstract 2336840.
Hawks, Richard L., "The Analysis of Cannabinoids in Biological Fluids," NIDA Research Monograph 42, 1982.
Hazekamp, Arno et al., "Cannabis; extracting the medicine," thesis/dissertation 2007.
"Information for health care professionals: *Cannabis* (marihuana, marijuana) and the cannabinoids," Health Canada, Feb. 2013.
Heishman, Stephen J. et al., "Effects of tetrahydrocannabinol content on marijuana smoking behavior, subjective reports, and performance," Pharmacology Biochemistry and Behavior, vol. 34, Issue 1, Sep. 1989, pp. 173-179, abstract.
Himes, Sarah K. et al., "Cannabinoids in exhaled breath following controlled administration of smoked cannabis," Clinical chemistry 59:12 1780-1789 (2013).
Huang, Wei et al., "Simultaneous determination of delta9-tetrahydrocannabinol and 11-nor-9-carboxy-delta9-tetrahydrocannabinol in human plasma by solid-phase extraction and gas chromatography-negative ion chemical ionization-mass spectrometry," Journal of Analytical Toxicology, vol. 25, Oct. 2001.
Huestis, Marilyn A. et al., "Blood cannabinoids. I. Absorption of THC and formation of 11-OH-THC and THCCOOH during and after smoking marijuana," Journal of Analytical Toxicology, vol. 16, Sep./Oct. 1992.
Huestis, Marilyn A. et al., "Blood cannabinoids. II. Models for the prediction of time of marijuana exposure from plasma concentraitons of delta9-tetrahydrocannabinol (THC) and 11-nor-9-carboxy-delta9-tetrahydrocannabinol (THCCOOH)," Journal of Analytical Toxicology, vol. 16, Sep./Oct. 1992.
Huestis, Marilyn A. et al., "Cannabinoid concentrations in hair from documented cannabis users," Forensic Sci Int. Jul. 4, 2007; 169(2-3): 129-136.
Johansson, E. et al., "Prolonged apparent half-life of delta 1-tetrahydrocannabinol in plasma of chronic marijuana users," J Pharm Pharmacol. May 1988;40(5):374-5, PubMed abstract 2899638.
Johannson, E. et al., "Terminal elimination plasma half-life of delta 1-tetrahydrocannabinol (delta 1-THC) in heavy users of marijuana," Eur J Clin Pharmacol. 1989;37(3):273-7, PubMed abstract 2558889.
Johansson, Eva et al., "Urinary excretion half-life of delta1-tetrahydrocannabinol-7-oic acid in heavy marijuana users after smoking," Journal of Analytical Toxicology, vol. 13, Jul./Aug. 1989.
Kadehijian, Leo, "Syva has been a leading developer and manufacturer of drugs-of-abuse tests for more than 30 years," Cannabinoid Issues: Passive inhalation, excretion patterns, and retention times, test result interpretation, Siemens Healthcare Diagnostics Inc., 2009.
Karst, Matthias et al., "Analgesic effect of the synthetic cannabinoid CT-3 on chronic neuropathic pain," JAMA. 2003;290(13):1757-1762.
Kelly, Peggy et al., "Metabolism of tetrahydrocannabinol in frequent and infrequent marijuana users," Journal of Analytical Toxicology, vol. 16, Jul./Aug. 1992.
Kemp, Philip M. et al., "Cannabinoids in Humans. II. The influence of three methods of hydrolysis on the concentration of THC and two metabolites in urine," Journal of Analytical Toxicology, vol. 19, Sep. 1995.

(56) References Cited

OTHER PUBLICATIONS

Kemp, Philip M. et al., "Cannabinoids in Humans. I. Analysis of delta9-tetrahydrocannabinol and six metabolites in plasma and urine using GC-MS," Journal of Analytical Toxicology, vol. 19, Sep. 1995.
Kidwell, David A. et al., "Testing for drugs of abuse in saliva and sweat," Journal of Chromatography B: Biomedical Sciences and Applications, vol. 713, Issue 1, Aug. 21, 1998, pp. 111-135, abstract.
Kintz, Pascal et al., "Detection of cannabis in oral fluid (saliva) and forehead wipes (sweat) from impaired drivers," Journal of Analytical Toxicology, vol. 24, Oct. 2000.
Kintz, Pascal et al., "Sweat testing for heroin and metabolites in a heroin maintenance program, " Clinical Chemistry 43:5, 736-739 (1997).
Kintz, P. et al., "Testing human hair for cannabis. II. Identification of TCD-COOH by GC-MS-NCI as a unique proof," J Forensic Sci. Jul. 1995;40(4):619-22, PubMed abstract 7595299.
Manno, Joseph E. et al., "Temporal indication of marijuana use can be estimated from plasma and urine concentrations of delta9-tetrahydrocannabinol, 11-hydroxy-delta9-tetrahydrocannabinol, and 11-nor-delta9-tetrahydrocannabinol-9-carboxylic acid," Journal of Analytical Toxicology, vol. 25, Oct. 2001.
Manolis, Antony et al., "The detection of delta9-tetrahydrocannabinol in the breath of human subjects," Clinical Biochem. 16,229 (1983).
"Marihuana '84," Proceedings of the Oxford Symposium on Cannabis, D.J. Harvy, editor, IRL Press, Oxford 1984.
Martin, B.R. et al., "3H-delta9-tetrahydrocannabinol distribution in pregnant dogs and their fetuses," Res Commun Chem Pathol Pharmacol. Jul. 1977;17(3):457-70, PubMed abstract 897339.
Mason, A.P. et al., "Cannabis: pharmacology and interpretation of effects," J Forensic Sci. Jul. 1985;30(3):615-31, PubMed abstract 2993473.
Mason, A.P. et al., "Ethanol, marijuana, and other drug use in 600 drivers killed in single-vehicle crashes in North Carolina, 1978-1981," J Forensic Sci. Oct. 1984;29(4):987-1026, PubMed abstract 6502125.
Matsunaga, T. et al., "Metabolism of delta 9-tetrahydrocannabinol by cytochrome P450 isozymes purified from hepatic microsomes of monkeys," Life Sci. 1995;56(23-24):2089-95, PubMed abstract 7776836.
Mattes, R.D. et al., "Bypassing the first-pass effect for the therapeutic use of cannabinoids," Pharmacol Biochem Behav. Mar. 1993;44(3):745-7, PubMed abstract 8383856.
Mattes, R.D. et al., "Cannabinoids and appetite stimulation," Pharmacol Biochem Behav. Sep. 1994;49(1):187-95, PubMed abstract 7816872.
McBurney, L.J. et al., "GC/MS and EMIT analyses for delta9-tetrahydrocannabinol metabolites in plasma and urine of human subjects," Journal of Analytical Toxicology, vol. 10, Mar./Apr. 1986.
Mechoulam, Raphael et al., "Cannabidiol: an overview of some chemical and pharmacological aspects. Part I: chemical aspects," Chemistry and Physics of Lipids 121 (2002) 35-43.
Mechoulam, Raphael, "Plant cannabinoids: a neglected pharmacological treasure trove," Br J Pharmacol. Dec. 2005; 146(7): 913-915.
Meier, H. et al., "Cannabis poisoning after eating salad," Schweiz Med Wochenschr. Feb. 8, 1997;127(6):214-8, PubMed abstract 9157527.
Menkes, D.B. et al., "Salivary THC following cannabis smoking correlates with subjective intoxication and heart rate," Psychopharmacology (Berl). 1991;103(2):277-9, PubMed abstract 1851311.
Mura, P. et al., "THC can be detected in brain while absent in blood," Letter to the Editor, Journal of Analytical Toxicology, vol. 29, Nov./Dec. 2005.
Nadulski T. et al., "Randomized, double-blind, placebo-controlled study about the effects of cannabidiol (CBD) on the pharmacokinetics of Delat9-tetrahydrocannabinol (THC) after oral application of THC verses standardized cannabis extract," Ther Drug Monit. Dec. 2005;27(6):799-810.

Nadulski T. et al., "Simultaneous and sensitive analysis of THC, 11-OH-THC, THC-COOH, CBD, and CBN by GC-MS in plasma after oral application of small doses of THC and cannabis extract," Journal of Analytical Toxicology, vol. 29, Nov./Dec. 2005.
Nahas, Gabriel G. et al., "Pharmacokinetics of THC in brain and testis, male gametotoxicity and premature apoptosis of spermatozoa," Human Psycopharmacology: Clinical and Experimental, vol. 17, Issue 2, pp. 103-113, Mar. 2002, abstract.
Niedbala, R. Sam et al., "Detection of marijuana use by oral fluid and urine analysis following single-dose administration of smoked and oral marijuana, " Journal of Analytical Toxicology, vol. 25, Jul./Aug. 2001.
Niedbala, R. Sam et al., "Passive cannabis smoke exposure and oral fluid testing. II. Two studies of extreme cannabis smoke exposure in a motor vehicle," Journal of Analytical Toxicology, vol. 29, Oct. 2005.
Ohlsson, A. et al., "Plasma delta-9 tetrahydrocannabinol concentrations and clinical effects after oral and intravenous administration and smoking," Clin Pharmacol Ther. Sep. 1980;28(3):409-16, PubMed abstract 6250760.
Ohlsson, Agneta et al., "Single dose kinetics of deuterium labelled delta1-tetrahydrocnnabinol in heavy and light cannabis users," Biological Mass Spectrometry, vol. 9, Issue 1, pp. 6-10, Jan. 1982, abstract.
Owens, S. Michael et al., I Radioimmunoassay of delta-9-tetrahydrocannabinol in blood and plasma with a solid-phase second-antibody separation method, Clin. Chem. 27/4, 619-624 (1981).
Peel, H.W. et al., "Detection of drugs in saliva of impaired drivers," J Forensic Sci. Jan. 1984;29(1):185-9, PubMed abstract 6366113.
Perez-Reyes, M. et al., "The clinical pharmacology and dynamics of marihuana cigarette smoking," J Clin Pharmacol. Aug.-Sep. 1981;21(8-9 Suppl):201S-207S, PubMed abstract 6271825.
Perez-Reyes, M. et al., "Comparison of effects of marihuana cigarettes to three different potencies," Clin Pharmacol Ther. May 1982;31(5):617-24, PubMed abstract 6280918.
Perez-Reyes, M. et al., "Intravenous injection in man of 9-tetrahydrocannabinol and 11-OH-9-tetrahydrocannabinol," Science. Aug. 18, 1972;177(4049):633-5, PubMed abstract 4558903.
Perez-Reyes, Mario, "Marijuana smoking: factors that influence the bioavailability of tetrahydrocannabinol," NIDA Monograph 1990;99:42.
Piao, Wen et al., "Development of azo-based fluorescent probes to detect different levels of hypoxia," Angew. Chem. Int. Ed. 2013, 52, 13028-13032.
Quintela, Oscar et al., "Recovery of drugs of abuse from the immunalysis quantisal™ oral fluid collection device," Journal of Analytical Toxicology, vol. 30, Oct. 2006.
Rahim S.A. et al., "Colorimetric determination of ethanol in the presence of methanol and other species in aqueous solution," Talanta. Nov. 1992;39(11):1489-91, PubMed abstract 18965558.
Rohrich, J. et al., "Concentrations of delta9-tetrahydrocannabinol and 11-nor-9-carboxytetrahydrocannabinol in blood and urine after passive exposure to cannabis smoke in a coffee shop," Journal of Analytical Toxicology, vol. 34, May 2010.
Russo, E. et al., "A tale of two cannabinoids: the therapeutic rational for combining tetrahydrocannabinol and cannabidiol," Med Hypotheses. 2006;66(2):234-46, PubMed abstract 16209908.
Samyn N. et al., "On-site testing of saliva and sweat with Drugwipe and determination of concentrations of drugs of abuse in saliva, plasma and urine of suspected users," Int J Legal Med. 2000;113(3):150-4, PubMed abstract 10876986.
Scheuplein, Robert J., "Mechanism of percutaneous absorption. II. Transient diffusion and the relative importance of various routes of skin penetration," J. Invest. Dermatol 1967;48:79.
Schwartz, Richard H. et al., "Laboratory detection of marijuana use, Experience with a photometric immunoassay to measure urinary cannabinoids," Aj J Dis Child. 1985;139(11):1093-1096, abstract.
Schwilke, Eugene W. et al., "Delta9-tetrahydrocannabinol (THC), 11-hydroxy-THC, and 11-nor-9-carboxy-THC plasma pharmacokinetics during and after continuous high-dose oral THC," Clinical Chemistry 55:12 2180-2189 (2009).

(56) References Cited

OTHER PUBLICATIONS

Shaw, Leslie M. et al., "Ultrasensitive measurement of delta-9-tetrahydrocannabinol with a high energy dynode detector and electron-capture negative chemical-ionization mass spectrometry," Clin. Chem. 37/12, 2062-2068 (1991).

Skopp, G. et al., "Partition coefficient, blood to plasma ratio, protein binding and short-term stability of 11-nor-Delta(9)-carboxy tetrahydrocannabinol glucuronide," Forensic Sci Int. Mar. 28, 2002;126(1):17-23, PubMed abstract 11955826.

Soares, J.R. et al., "Significant developments in radioimmune methods applied to delta9-THC and its 9-substituted metabolites," Analysis of Cannabinoids Research Monograph 42, NIDA 1982.

Stinchcomb, a.L. et al., "Human skin permeation of Delta8-tetrahydrocannabinol, cannabidiol and cannbinol," J Pharm Pharmacol. Mar. 2004;56(3):291-7, PubMed abstract 15025853.

Strano-Rossi, Sabina et al., "Analysis of stimulants in oral fluid and urine by gas chromatography-mass spectrometry II: Pseudophedrine," Journal of Analytical Toxicology, vol. 34, May 2010.

Tan, Chongxiao et al., "Direct detection of delta9-tetrahydrocannabinol in aqueous samples using a homogeneous increasing fluorescence immunoassay (HiFi)," Anal Bioaanal Chem, 2010. 8 pgs.

Teshima, N. et al, "Determination of acetone in breath", Analytica Chimica Acta, 2005, 535, pp. 189-199.

Toennes, Stefan W. et al., "Pharmacokinetic properties of delta9-tetrahydrocannabinol in oral fluid of occasional and chronic users," Journal of Analytical Toxicology, vol. 34, May 2010.

Turner, Carton E. et al., "Constituents of *Cannabis sativa* L. XVII. A review of the natural constituents," J. Nat. Prod. 1980;43:169.

Valiveti, S. et al., "In vitro/in vivo correlation studies for transdermal delta 8-THC development," J Pharm Sci. May 2004;93(5):1154-64, PubMed abstract 15067692.

Van der Kooy, F. et al., "Cannabis smoke condensate I: The effect of different preparation methods on tetrahydrocannabinol levels," Inhalation Toxicology, 20:801-804, 2008.

Vinciguerra, V. et al., "Inhalation marijuana as an antiemetic for cancer chemotherapy," NY State J Med. Oct. 1988;88(10):525-7.

Wall, M.E. et al., "The metabolism of delta 9-tetrahydrocannabinol and related cannabinoids in man," J Clin Pharmacol. Aug.-Sep. 1981;21 (8-9 Suppl):178S-189S, PubMed abstract 6271823.

Wall, M.E. et al., "Metabolism, disposition, and kinetics of delta-9-tetrahydrocannabinol in men and women," Clin Pharmacol Ther. Sep. 1983;34(3):352-63, PubMed abstract 6309462.

Walsh, J. Michael et al., "An evaluation of rapid point-of-collection oral fluid drug-testing devices," Journal of Analytical Toxicology, vol. 27, Oct. 2003.

Watanabe, K. et al., "Brain microsomal oxidation of delta 8- and delta 9-tetrahydrocannabinol," Biochem Biophys Res Commun. Nov. 30, 1988;157(1):75-80, PubMed abstract 2848522.

Widman, M. et al., "Metabolism of delta 1-tetrahydrocannabinol by the isolated perfused dog lung. Comparison with in vitro liver matabolism." J Phar Pharmacol. Nov. 1975;27(11):842-8, PubMed abstract 1493.

Williams, P.L. et al., "Identification in human urine of delta 9-tetrahydrocannabinol-11-oic acid glucuronide: a tetrahydrocannabinol metabolite," J Pharm Pharmacol. Jul. 1980;32(7):445-8, PubMed abstract 6105177.

Wingert, William E., "Lowering cutoffs for initial and confirmation testing for cocaine and marijuana: large-scale study of effects on the rates of drug-positive results," Clinical Chemistry 43:1 100-103 (1997).

Zajicek, J. et al., "Cannabinoids for treatment of spasticity and other symptoms related to multiple sclerosis (CAMS study): multicentre randomised placebo-controlled trial," Lancet. Nov. 8, 2003;362(9395):1517-26, abstract.

Zias, Joe et al., "Early medical use of cannabis," Nature; May 20, 1993; 363,6426; Research Library Core p. 215.

Zuardi, A.W. et al., "Action of cannabidiol on the anxiety and other effects produced by delta 9-THC in normal subjects," Psychopharmacology (Berl). 1982;76(3):245-50, PubMed abstract 6285406.

U.S. Appl. No. 15/650,518, filed Jul. 14, 2017, Michael J. Gordon et al.

U.S. Appl. No. 15/650,537, filed Jul. 14, 2017, Michael J. Gordon et al.

U.S. Appl. No. 14/641,412, filed Mar. 8, 2015, Michael Scott Lynn et al.

U.S. Appl. No. 15/217,151, filed Jan. 19, 2018, Michael Scott Lynn et al.

U.S. Appl. No. 15/217,264, filed Jul. 22, 2016, Michael Scott Lynn et al.

U.S. Appl. No. 15/650,518, Office Action dated Oct. 4, 2017.
U.S. Appl. No. 15/650,518, Notice of Allowance dated Feb. 1, 2018.
U.S. Appl. No. 14/641,412, Office Action dated May 19, 2016.
U.S. Appl. No. 14/641,412, Final Office Action dated Dec. 5, 2016.
U.S. Appl. No. 14/641,412, Office Action dated Jun. 26, 2017.
U.S. Appl. No. 14/641,412, Notice of Allowance dated Jan. 9, 2018.
U.S. Appl. No. 15/217,151, Office Action dated Jan. 9, 2017.
U.S. Appl. No. 15/217,151, Office Action dated May 16, 2017.
U.S. Appl. No. 15/217,151, Final Office Action dated Oct. 30, 2017.
U.S. Appl. No. 15/217,151, Notice of Allowance dated Dec. 22, 2017.
U.S. Appl. No. 15/217,264, Office Action dated Oct. 24, 2016.
U.S. Appl. No. 15/217,264, Office Action dated Mar. 20, 2017.
U.S. Appl. No. 15/217,264, Final Office Action dated Aug. 16, 2017.
U.S. Appl. No. 15/217,264, Notice of Allowance dated Nov. 16, 2017.
U.S. Appl. No. 14/641,412, Corrected Notice of Allowability dated Apr. 18, 2018.

Huestis, Marilyn A. et al., "Alternative testing matrices," chapter 11 of the Drug Abuse Handbook, 1998 CRC Press LLC, ISBN 0-8493-2637-0.

Huestis, M.A. et al., "Characterization of the absorption phase of marijuana smoking," Clin Pharmacol Ther. Jul. 1992;52(1):31-41, PubMed abstract 1320536.

Huestis, Marilyn A. et al., "Detection times of marijuana metabolites in urine by immunoassay and GC-MS," Journal of Analytical Toxicology, vol. 19, Oct. 1995.

Huestis, Marilyn A. et al., "Differentiating new marijuana use from residual drug excretion in occasional marijuana users," Journal of Analytical Toxicology, vol. 22, Oct. 1998.

Huestis, Marilyn A. et al., "Estimating the time of last cannabis use from plasma delta9-tetrahydrocannabinol and 11-nor-9-carboxy-delta9-tetrahydrocannabinol concentrations," Clinical Chemistry 51:12 2289-2295 (2005).

Huestis, Marilyn A., "Human cannabinoid pharmacokinetics," Chem Biodivers. Aug. 2007; 4(8): 1770-1804.

Huestis, Marilyn A. et al., "Relationship of delta9-tetrahydrocannabinol concentrations in oral fluid and plasma after controlled administration of smoked cannabis," Journal of Analytical Toxicology, vol. 28, Sep. 2004.

Huestis, Marilyn A. et al., "Urinary excretion profiles of 11-nor-9-carboxy-delta9-tetrahydrocannabinol in humans after single smoked doses of marijuana," Journal of Analytical Toxicology, vol. 20, Oct. 1996.

Hunt, C.A. et al., "Evidence that cannabidiol does not significantly alter the pharmacokinetics of tetrahydrocannabinol in man," J Pharmacokinet Biopharm. Jun. 1981;9(3):245-60, PubMed abstract 6270295.

Hunt, C.A. et al., "Tolerance and disposition of tetrahydrocannabinol in man," J Pharmacol Exp Ther. Oct. 1980;215(1):35-44, PubMed abstract 6256518.

Iribarne, C. et al., "Involvement of cytochrome P450 3A4 enzyme in the N-demethylation of methadone in human liver microsomes," Chem Res Toxicol. Mar. 1996;9(2):365-73, PubMed abstract 8839037.

Jehanli, A. et al., "Blind trials of an onsite saliva drug test for marijuana and opiates," J Forensic Sci. Sep. 2001;46(5):1214-20, PubMed 11569567.

Joern, William A., "Surface adsorption of the urinary marijuana carboxy metabolite: the problem and a partial solution," Letter to the Editor, Journal of Analytical Toxicology, vol. 16, Nov./Dec. 1992.

(56) References Cited

OTHER PUBLICATIONS

Johansson, E. et al., "Determination of delta 1-tetrahydrocannabinol in human fat biopsies from marihuana users by gas chromatography-mass spectrometry," Biomed Chromatogr. Jan. 1989;3(1):35-8, PubMed abstract 2539872.

Kovatsi, Leda et al., "Development and validation of a high-performance liquid chromatography method for the evaluation of niflumic acid cross-reactivity of two commercial immunoassays for cannabinoids in urine," Journal of Analytical Toxicology, vol. 34, May 2010.

Kreuz, D.S. et al., "Delta-9-tetrahydrocannabinol: localization in body fat," Science, Jan. 26, 1973;179(4071):391-3, PubMed abstract 4682965.

Krishna, D.R. et al., "Extrahepatic metabolism of drugs in humans," Clin Pharmacokinet. Feb. 1994;26(2):144-60, PubMed abstract 8162658.

Lafolie, P. et al., "Importance of creatinine analyses of urine when screening for abused drugs," Clin. Chem. 37/11, 1927-1931 (1991).

Laloup, M. et al., "Correlation of delta9-tetrahydrocannabinol concentrations determined by LC-MS-MS in oral fluid and plasma from impaired drivers and evaluation of the on-site Drager Drug Test," Forensic Sci Int. 2006 SRP 12;161(2-3):175-9, PubMed abstract 16842950.

Law, B. et al., "Forensic aspects of the metabolism and excretion of cannabinoids following oral ingestion of cannabis resin," J Pharm Pharmacol. May 1984;36(5):289-94, PubMed abstract 6145762.

Lee, Sooyeun et al., "Estimation of the measurement uncertainty by the bottom-up approach for the determination of methamphetamine and amphetamine in urine," Journal of Analytical Toxicology, vol. 34, May 2010.

Lemberger, L. et al., "11-hydroxy-9-tetrahydrocannabinol: pharmacology, disposition, and metabolism of a major metabolite of marihuana in man," Science. Jul. 7, 1972;177(4043):62-4, PubMed abstract 5041775.

Lemberger, L. et al., "Delta-9-tetrahydrocannabinol: metabolism and disposition in long-term marihuana smokers," Science. Jul. 2, 1971;173(3991):72-4, PubMed abstract 5087483.

Lemberger, L. et al., "Marihuana: studies on the disposition and metabolism of delta-9-tetrahydrocannabinol in man," Science. Dec. 18, 1970;170(3964):1320-2, PubMed abstract 5479011.

Lindgren, J.E. et al., "Clinical effects and plasma levels of delta 9-tetrahydrocannabinol (delta 9-THC) in heavy and light users of cannabis," Psychopharmacology (Berl). 1981;74(3):208-12, PubMed 6267648.

Malfait, A.M. "The nonpsychoactive cannabis constituent cannabidiol is an oral anti-arthritic therapeutic in murine collagen-induced arthritis," Proc Natl Acad Sci USA Aug. 15, 2000;97(17):9561-9566.

Mijuriya, Tod H., "Cannabis as a substitute for alcohol: a harm-reduction approach," Journal of Cannabis Therapeutics, vol. 4(1) 2004.

Milman, Garry et al., "Simultaneous quantification of cannabinoids and metabolites in oral fluid by two-dimensional gas chromatography mass spectrometry," J Chromatogr A. Feb. 26, 2010; 1217(9): 1513-1521.

Moeller, M.R. et al., "Simultaneous quantitation of delta-9-tetrahydrocannabinol (THC) and 11-nor-9-carboxy-delta-9-tetrahydrocannabinol (THC-COOH) in serum by GC/MS using deuterated internal standards and its application to a smoking study and forensic cases," J Forensic Sci. Jul. 1992;37(4):969-83, PubMed abstract 1324293.

Moldoveanu, Serban C. et al., "Differences in the chemical composition of the particulate phase of inhaled and exhaled cigarette mainstream smoke," Contributions to Tobacco Research 22(4), 290 (2007).

Moore, Christine et al., "Analytical procedure for the determination of the marijuana metabolite 11-nor-delta9-tetrahydrocannabinol-9-carboxylic acid in oral fluid specimens," Journal of Analytical Toxicology, vol. 30, Sep. 2006.

Moore, Christine et al., "Application of two-dimensional gas chromatography with electron capture chemical ionization mass spectrometry to the detection of 11-nor-delta9-tetrahydrocannabinol-9-carboxylic acid (THC-COOH) in hair," Journal of Analytical Toxicology, vol. 30, Apr. 2006.

Moore, Christine et al., "Detection of the marijuana metabolite 11-nor-delta9-tetrahydrocannabinol-9-carboxylic acid in oral fluid specimens and its contribution to positive results in screening assays," Journal of Analytical Toxicology, vol. 30, Sep. 2006.

Moore, Christine et al., "The determination of 11-nor-delta9-tetrahydrocannabinol-9-carboxylic acid (THC-COOH) in hair using negative ion gas chromatography-mass spectrometry and high-volume injection," Journal of Analytical Toxicology, vol. 25, Oct. 2001.

Morland, J. et al., "Cannabinoids in blood and urine after passive inhalation of cannabis smoke," J Forensic Sci. Oct. 1985;30(4):997-1002, PubMed abstract 2999292.

Mule, S.J. et al., "Active and realistic passive marijuana exposure tested by three immunoassays and GC/MS in urine," Journal of Analytical Toxicology, vol. 12, May/Jun. 1988.

Mura, P. et al., "Evaluation of six rapid tests for screening of cannabis in sweat, saliva and tears," Acta Clin Belg. 1999;53 Suppl 1:35-8, PubMed abstract 10216980.

* cited by examiner

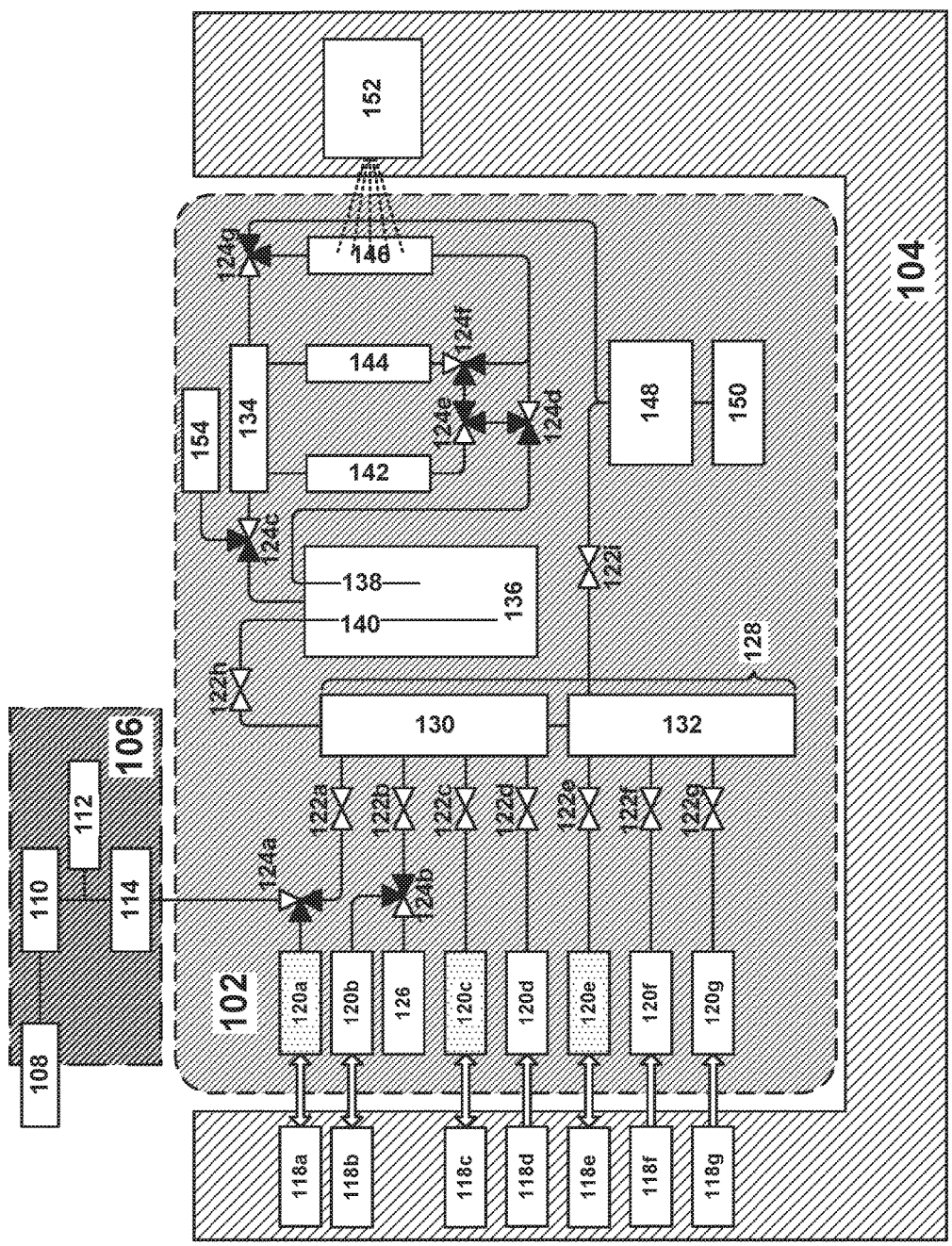

COMPOSITIONS AND METHODS FOR DETECTION OF TARGET CONSTITUENT IN EXHALED BREATH

CROSS REFERENCE TO RELATED APPLICATIONS

This application is a continuation of U.S. patent application Ser. No. 15/217,151, filed Jul. 22, 2016, titled "COMPOSITIONS AND METHODS FOR DETECTION OF TARGET CONSTITUENT IN EXHALED BREATH," now allowed, which claims priority benefit under 35 U.S.C. § 119(e) to U.S. Provisional Application No. 62/351,858, filed Jun. 17, 2016, titled "COMPOSITIONS AND METHODS FOR DETECTION OF TARGET CONSTITUENT IN EXHALED BREATH," which are also hereby incorporated by reference herein in their entireties.

U.S. patent application Ser. No. 14/997,405, titled "METHOD, DEVICE AND SYSTEM FOR TARGET SUBSTANCE DETECTION" and filed Jan. 15, 2016, which claims priority benefit under 35 U.S.C. § 119(e) to U.S. Provisional Application Nos. 62/104,813, filed Jan. 18, 2015, and 62/107,331, filed Jan. 23, 2015, both of which are titled "METHOD, DEVICE AND SYSTEM FOR TARGET SUBSTANCE DETECTION," as well as U.S. Provisional Application Nos. 62/277,854, filed Jan. 12, 2016, and titled "PORTABLE, HAND-HELD INSTRUMENT FOR DETECTION AND QUANTIFICATION OF CANNABINOIDS AND ALCOHOL IN EXHALED HUMAN BREATH," 62/337,286, filed May 16, 2016, and titled "BREATH COLLECTOR MODULE," and 62/351,821 filed Jun. 17, 2016, and titled "SYSTEM AND METHOD FOR TARGET SUBSTANCE IDENTIFICATION," are all hereby incorporated by reference herein in their entireties.

FIELD OF THE INVENTION

The present disclosure relates generally to labeling, detection and measurement of target substances in exhaled human breath.

BACKGROUND

With legalization of marijuana expanding and the risk of marijuana-associated impaired driving increasing, reliable techniques for detection of marijuana impairment are needed. It is anticipated by the present inventors that there will be an increased need for detection methods and associated compositions that are adaptable to portable and accurate measurement devices for quantifying levels of cannabinoid compounds, such as tetrahydrocannabinol (THC), that are present in a person's breath, e.g., such as during a traffic stop for suspected driving-under-the-influence. THC detection poses significant challenges since the amounts of THC that may be present in an exhaled breath are quite minute—much more so than is the case with alcohol. Furthermore, THC detection in human breath is generally the only reliable way to determine if a suspected marijuana user is under the influence. Unlike with alcohol, which the body can purge in relatively short order, e.g., less than a day, THC compounds may be present in a person's body long after they are no longer under the influence of the THC. Thus, detection of THC via blood or urine sample may result in false positives. Testing for THC in breath at the roadside would be convenient, non-invasive, and leverages the wide acceptance of administering a breath test at the roadside, as is commonly employed for alcohol.

SUMMARY

Chemical compositions and methods provide labeling, detection and measurement of target substances in exhaled human breath, and can be implemented in connection with a handheld device—much like a Breathalyzer portable breath testing unit for alcohol—to support rapid quantification of levels of cannabinoid compounds, such as tetrahydrocannabinol (THC), of suspected users at the roadside. In some implementations, roadside detection and quantification of multiple substances, for example THC and alcohol, is obtained from a breath sample taken using a handheld device.

Quantitative detection of THC in human breath is challenging due to the extremely low concentration of THC in human breath and the presence of many common, similarly structured contaminants or chemical interferences. As disclosed herein, breath constituents from one or more (e.g., 1-3) exhalations may be captured as a sample, processed and analyzed to detect the presence and level of constituents, in particular THC. In one aspect, a method of detecting THC in exhaled breath involves capturing an exhaled breath sample, forming a fluorescent-labeled sample adduct with THC in the captured breath sample in a sample adduct solution, isolating the fluorescent-labeled THC sample adduct from aqueous media, activating the fluorescent-labeled THC sample adduct's fluorophore, and detecting by determining an amount of THC in the captured breath sample based on the measured fluorescence of the isolated and activated fluorescent-labeled THC sample adduct.

A method of detecting THC in exhaled breath may be characterized as another embodiment. The method involves capturing an exhaled breath sample by adsorption and elution, forming a fluorescent-labeled sample adduct with THC in the captured breath sample in a basic buffered sample adduct solution, adding to the sample adduct solution a second solvent and mixing to form a mixture, separating the mixture into polar and nonpolar phase layers, the nonpolar layer containing the fluorescent-labeled THC sample adduct, and detecting by exposing the sample adduct in the nonpolar phase to a light source to produce a fluorescence, measuring the fluorescence, and determining a quantity of THC captured and collected from the breath sample based on the measured fluorescence of the sample adduct in the nonpolar phase.

In accordance with either of these embodiments, THC in a breath sample can be captured by adsorption on a catch medium or catch media. The breath sample may be taken, for example, with a handheld device suitable for roadside use. THC in a breath sample taken with the device can be captured by adsorption on a catch medium or catch media. THC adsorbed on the catch medium may be eluted from the capture medium using a first solvent. A basic buffer and an aqueous diazotized fluorophore solution may then be added to the capture solution to form a fluorescent-labeled THC adduct in a sample adduct solution.

After formation of the adduct solution, the fluorescent-labeled THC adduct is separated from the aqueous components of the sample adduct solution. A second solvent may be added to the sample adduct solution, the resulting mixture vigorously mixed, and the mixture then allowed to separate into polar and nonpolar phase layers. Any fluorescent-labeled THC-adduct will be contained in the nonpolar layer, and thereby isolated by solvent extraction from molecular species that dissolve in polar, but not nonpolar solvents.

In various implementations, the first and/or second solvents can be organic solvents, the diazotized fluorophore solution is aqueous, and at least one of the first and second solvents is a nonpolar solvent immiscible with water. For example, in some implementations the first solvent is a polar organic solvent miscible with water and the second solvent is a nonpolar organic solvent immiscible with water. Also in various implementations, the diazotized fluorophore solution is acidic with an acid strength such that the pH of the adduct solution remains basic by the action of the basic buffer.

Once the sample adduct, if any, is isolated in the nonpolar fraction of the solvent extraction, it can then be detected and quantified by optical techniques, for example by exposure to a light source and then measuring the fluorescence of the fluorescent-labeled adduct and determining a quantity of any THC captured from the original breath sample based on the measured fluorescence. In various embodiments, data corresponding to the determined quantity of THC may be wirelessly transmitted to a remote location by any suitable technique.

In various implementations, prior to the exposing the sample adduct to the light source, the fluorophore is activated. The fluorophore is activated by introducing charge into the sample adduct nonpolar phase. For example, charge may be introduced into the sample adduct nonpolar phase by routing the adduct nonpolar phase through a charge-donating conduit prior to exposure to the light source (e.g., acid-washed glass or uncoated hydrophobic polypropylene material (e.g., Repel Polymer Technology (RPT) pipette tip)), and/or applying a voltage to the sample adduct nonpolar phase. In other embodiments, charge may be introduced into the sample adduct nonpolar phase by adding acid to the mixture prior to solvent extraction to isolate the sample adduct in the nonpolar phase.

In various implementations, prior to the exposing the adduct to the light source, the adduct is separated from non-target molecular species and fluorescence strength of the fluorophore is improved by removing the nonpolar phase from the polar phase following solvent extraction.

These and other aspects of this disclosure are described and features thereof are illustrated by way of example in the description that follows.

BRIEF DESCRIPTION OF THE DRAWINGS

FIG. 3 depicts a schematic of an example target substance analysis system in conjunction with which the methods and compositions described and claimed herein may be implemented.

DETAILED DESCRIPTION

Chemical compositions and methods provide labeling, detection and measurement of target substances in exhaled human breath, and can be implemented in connection with a handheld device—much like a Breathalyzer portable breath testing unit for alcohol—to support rapid quantification of levels of cannabinoid compounds, such as tetrahydrocannabinol (THC), of suspected users at the roadside. In some implementations, roadside detection and quantification of multiple substances, for example THC and alcohol, is obtained from a breath sample taken using a handheld device.

Figure 1:
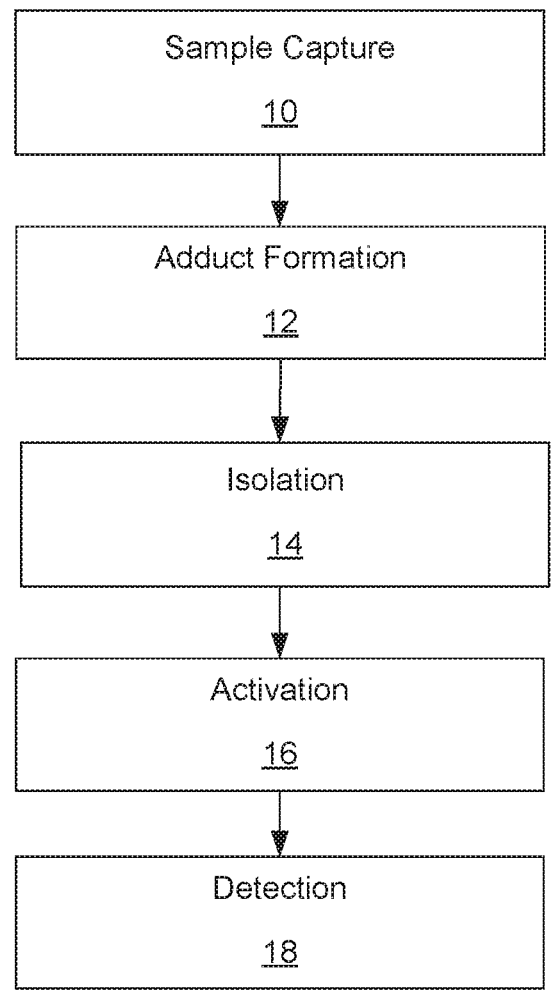
FIGS. 1 and 2 depict process flow charts for methods in accordance with the present disclosure.

Quantitative detection of THC in human breath is challenging due to the extremely low concentration of THC in human breath and the presence of many common, similarly structured contaminants or chemical interferences. As disclosed herein, breath constituents from one or more (e.g., 1-3) exhalations may be captured as a sample, processed and analyzed to detect the presence and level of constituents, in particular THC. FIG. 1 depicts a flow chart showing operations in such a method. It should be understood that methods in accordance with this disclosure may be practiced with various permutations, and with or possibly without all of the operations described with reference to FIG. 1, and other operations may be conducted in some embodiments, such as are otherwise described herein, for example.

Referring to FIG. 1, a method of detecting THC in exhaled breath in accordance with one embodiment is shown. The method includes capturing an exhaled breath sample (10), forming a fluorescent-labeled sample adduct with THC in the captured breath sample in a sample adduct solution (12), isolating the fluorescent-labeled THC sample adduct from aqueous media (14), activating the fluorescent-labeled THC sample adduct fluorophore (16), and detecting by determining an amount of THC in the captured breath sample based on the measured fluorescence of the isolated and activated fluorescent-labeled THC sample adduct (18).

Figure 2:
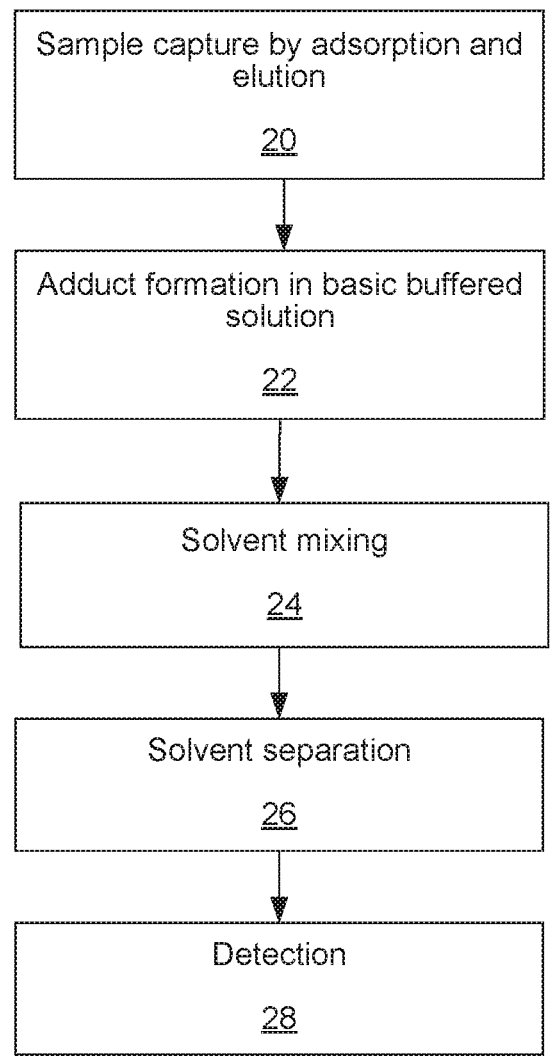

Referring to FIG. 2, a method of detecting THC in exhaled breath characterized as another embodiment is shown. The method includes capturing an exhaled breath sample by adsorption and elution (20), forming a fluorescent-labeled sample adduct with THC in the captured breath sample in a basic buffered sample adduct solution (22), adding to the sample adduct solution a second solvent and mixing to form a mixture (24), separating the mixture into polar and nonpolar phase layers, the nonpolar layer containing the fluorescent-labeled THC sample adduct (26), and detecting by exposing the sample adduct in the nonpolar phase to a light source to produce a fluorescence, measuring the fluorescence, and determining a quantity of THC captured and collected from the breath sample based on the measured fluorescence of the sample adduct in the nonpolar phase (28).

In accordance with the embodiments depicted in either FIG. 1 or 2, THC in a breath sample can be captured by adsorption on a catch medium or catch media. The breath sample may be taken, for example, with a handheld device suitable for roadside use. Suitable breath sample capture apparatus and media are described in Provisional Application No. 62/337,286, filed May 16, 2016, and titled "BREATH COLLECTOR MODULE," incorporated by reference herein for the disclosure of these features. As described therein, the catch media may be contained within a breath capture module that includes a mouthpiece into which a subject can exhale a breath sample, a saliva trap downstream of the exhaled breath flow, and a porous medium or media contained in a passage downstream of the saliva trap. The porous catch media may take a number of different forms. For example, the porous media may be composed of discrete granules, beads, or particles that may be retained in the passage by permeable mesh screens or other porous bulkheads. In some implementations, the porous media may include silica microbeads having a size of between 10 microns to 5 mm in size (diameter or maximum dimension). In some implementations, the size of the silica microbeads may be between 400 µm and 1500 µm, or 600 µm and 800 µm or a size of between 800 µm and 1000 µm. In some implementations, the silica beads are longer in one dimension than the other, or cubic, spherical, or cylindrical. In some implementations, the silica microbeads may be packed in a volume of from about from 0.1 mL to 10 mL, For example, in some implementations, the beads are substantially spherical, between 800 μm and 1000 μm in diameter packed in a volume of about 0.5 mL. Performance, including facilitation of adsorbed material recovery from the silica beads in the subsequent elution operation, may be enhanced by washing or otherwise moistening the beads with water prior to capturing a breath sample. Materials other than or in addition to silica may be used as well, including, for example, one or more of filter paper, activated charcoal granules, glass wool, layered mesh screens, or frits, e.g., sintered frits.

THC adsorbed on the catch medium may be eluted from the capture medium using a solvent to form a capture solution. A basic buffer and a diazotized fluorophore solution may then be added to the capture solution to form a fluorescent-labeled THC adduct in a sample adduct solution.

After formation of the sample adduct solution, the fluorescent-labeled THC adduct is separated from polar (e.g., aqueous) components of the sample adduct solution. A second solvent may be added to the sample adduct solution, the resulting mixture mixed, preferably vigorously to obtain short path lengths to expedite the diffusion of the adduct into the nonpolar solvent, and the mixture then allowed to separate into polar and nonpolar phase layers. Any fluorescent-labeled THC-adduct will be contained in the nonpolar layer, and thereby isolated by solvent extraction from molecular species that dissolve in polar, but not nonpolar solvents.

In various implementations, the first (elution) and/or second solvents can be organic solvents, the diazotized fluorophore solution is aqueous, and at least one of the first and second solvents is a nonpolar solvent immiscible with water. In some implementations the first solvent is a polar organic solvent miscible with water and the second solvent is a nonpolar organic solvent immiscible with water. Suitable examples of the first polar solvent are alcohols, for example ethanol. Suitable examples of the second nonpolar solvent are alkanes, including ethers. For example, the nonpolar organic solvent may include heptane and methyl tertiary butyl ether (MTBE) in proportions from about 15-50% by volume MTBE with the balance heptane, such as 75 vol % heptane and 25 vol % MTBE.

In various embodiments, the basic buffer buffers the sample adduct solution to a pH between about 9 and 11, or between about 9.5 and 10. Suitable examples of the basic buffer include $NaHCO_3$ and $Na_2CO_3$, for example about 60 mol % $NaHCO_3$ and 40 mol % $Na_2CO_3$, although a wide variety of well-known buffers may also be suitable.

Also in various implementations, the added diazotized fluorophore solution is acidic with an acid strength such that the pH of the sample adduct solution remains basic by the action of the basic buffer.

In various embodiments, the diazotized fluorophore has the formula:

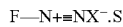

wherein:
F is a functionalized fluorophore;
$N+\equiv N$ is a diazo functional group;
$X^-$ is a negatively charged ion balancing the charge on the diazo functional group; and
S is a diazo functional group stabilizer.

F can be an amine-functionalized fluorophore, such as a primary amine-functionalized fluorophore. The fluorophore can be any one of: xanthene, cyanine, naphthalene, coumarin, oxadiazole, anthracene, pyrene, oxazine, acridine, arylmethine, tetrapyrrole, green fluorescent protein, red fluorescent protein, yellow fluorescent protein, cadmium selenide quantum dot, cadmium selenide/zinc sulfide alloy quantum dot, cadmium selenide sulfide quantum dot, cadmium selenide sulfide/zinc sulfide alloy quantum dot, cadmium telluride quantum dot, cadmium sulfide quantum dot, lead sulfide quantum dot, or indium phosphide/zinc sulfide alloy quantum dot derivatives, and mixtures thereof. In particular examples, the fluorophore is a xanthene, for example a rhodamine, for example rhodamine 123, for example rhodamine 123 diazotized at a primary amine group.

The $F—N+\equiv N$ group of a suitable diazotized fluorophore is selected to bind to a cannabinoid. In various embodiments, the $F—N+\equiv N$ binds to the para or ortho position of a phenol ring of tetrahydrocannabinol forming an $N=N$ azo bond such that an adduct is formed having the formula:

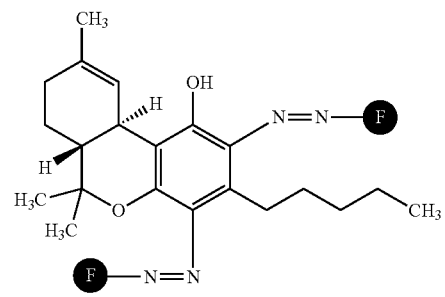

wherein:
F is the functionalized fluorophore, and only one or the other $—N=N—F$ group is present.

The acidic diazotized fluorophore solution is formed from constituent materials in an acidic solution. For example, the acidic solution may contain dilute HCl, such as 100 μM HCl. Indicators/labels containing stabilized $N^+\equiv N$ diazo functional groups can be been synthesized to rapidly (e.g., <2 min) and selectively bind to THC and/or derivatives thereof at the para or ortho position of the phenol ring forming an $N=N$ azo bond. The binding produces a chemically bonded fluorescent-labeled THC adduct. The diazotized fluorophore indicator/label is generally of the form:

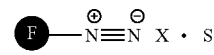

where:
F is a fluorophore, examples of which may include xanthene, cyanine, naphthalene, coumarin, oxadiazole, anthracene, pyrene, oxazine, acridine, arylmethine, tetrapyrrole, green fluorescent protein, red fluorescent protein, yellow fluorescent protein, cadmium selenide quantum dot, cadmium selenide/zinc sulfide alloy quantum dot, cadmium selenide sulfide quantum dot, cadmium selenide sulfide/zinc sulfide alloy quantum dot, cadmium telluride quantum dot, cadmium sulfide quantum dot, lead sulfide quantum dot, or indium phosphide/zinc sulfide alloy quantum dot derivatives, or any combination thereof;
$N^+\equiv N$ is a diazo-functional group that is chemically bonded/grafted/functionalized/conjugated to F;
$X^-$ is a negatively charged ion that charge balances the positively charged diazo functional group $N^+\equiv N$, examples of which may include fluoride, sulfide, chloride, nitride, bromide, iodide, arsenate, phosphate, arsenite, hydrogen phosphate, dihydrogen phosphate, sulfate, nitrate, hydrogen sulfate, nitrite, thiosulfate, sulfite, perchlorate, iodate, chlorate, bromate, chlorite, hypochlorite, hypobromite, carbonate, chromate, hydrogen carbonate, dichromate, acetate, formate, cyanide, amide, cyanate, peroxide, thiocyanate, oxalate, hydroxide, or permanganate ion derivatives, or any combination thereof;

S is a $N^+{\equiv}N$ stabilizer, for prevention of decomposition of the diazo compound, composed of salts and/or polymers, examples of which may include tin chloride, cadmium chloride, manganese chloride, zinc chloride, sodium fluoroborate, aromatic, aliphatic, or heterocyclic sulfonic acids, sulfates, and chlorides, polymers with free terminal halo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, orthoester, methylenedioxy, orthocarbonate ester, amide, amine, ammonium, imine, imide, azide, azo, diazo, cyanate, nitrate, nitrile, nitro, pyridine, thiol, sulfide, disulfide, sulfoxide, sulfone, sulfinic acid, sulfonic acid, camphosulphonic acid, thiocyanate, thione, thial, sulfonyl chloride, carbonyl chloride, phosphine, phosphonic acid, phosphate, phosphodiester, boronic acid, boronic ester, boronic acid, borinic ester, or any combination thereof.

Indicators including stabilized $N^+{\equiv}N$ diazo functional groups can be synthesized, for example, by a process including the combination of a primary amine ($-NH_2$) functionalized fluorophore, F (listed above), in an acidic solution ($H^+X^-$) with sodium nitrite ($NaNO_2$) and stabilizers, S (listed above):

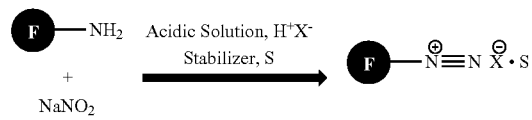

Acidic solutions may include any negatively charged ion $X^-$ (such as those listed above) charge balanced with a positively charged hydrogen ion $H^+$, in a solvent that has been chosen for suitable or optimal reaction conditions, examples of which include pentane, cyclopentane, hexane, cyclohexane, benzene, toluene, 1,4-dioxane, chloroform, diethyl ether, dichloromethane, tetrahydrofuran, ethyl acetate, acetone, dimethylformamide, acetonitrile, dimethyl sulfoxide, nitromethane, propylene carbonate, formic acid, n-butanol, isopropanol, n-propanol, n-octanol, ethanol, methanol, acetic acid, water, hydrochloric acid, nitric acid, sulfuric acids, propanoic acid, trifluoroacetic acid, perchloric acid, boric acid, p-toluene sulfonic acid, pyridine, methyl isobutyl ketone, isooctane, carbon disulfide, carbon tetrachloride, o-xylene, m-xylene, p-xylene, petroleum ether, heptane, diethyl amine, triethyl amine, tert-butyl methyl ether, tert-butyl alcohol, isobutyl alcohol, methyl ethyl ketone, isoamyl alcohol, diethyl ketone, dimethoxyethane, butyl acetate, 1-chlorobutane, hexamethylphosphorous triamide, 2-ethoxyethyl ether, N,N-dimethylacetimide, ethylene glycol, diethylene glycol, glycerin, diethylene glycol dimethyl ether, 2-methoxyethanol, 2-methoxylethyl acetate, benzonitrile, 1-methyl-2-pyrrolidinone, hexamethylphosphoramide, acetic anhydride, chlorobenzene, propylene carbonate, 1,2-dichloroethane, 1,2-dichlorobenzene, 2,2,2-trifluoroethanol, 1,1,2-trichlorotrifluoroethane, tetrachloroethylene, or any combination thereof.

Thus, in various embodiments, this disclosure also provides, a method of making a fluorescent-labeled THC-adduct including the operations of combining a primary amine-functionalized fluorophore, sodium nitrite and a diazo functional group stabilizer to form an aqueous solution of a diazo-functionalized fluorophore reactant, the fluorophore reactant solution having an acidic pH; forming a THC solution by dissolving THC in a polar organic solvent; buffering the THC solution by adding a basic buffer to the THC solution; combining the fluorophore reactant solution with the buffered THC solution to form a fluorescent-labeled THC-adduct solution, the adduct solution having a basic pH in the range of about 9-11, for example as depicted below:

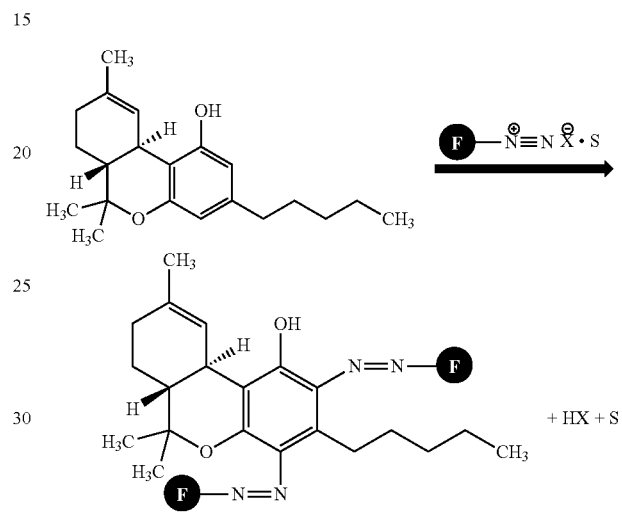

Returning to the processes of FIGS. 1 and 2, once the sample adduct, if any, is isolated in the nonpolar fraction of the solvent extraction, it can then be detected and quantified by optical techniques, for example by exposure to a light source and then measuring the fluorescence of the fluorescent-labeled adduct and determining a quantity of any THC captured from the original breath sample based on the measured fluorescence. The detection using optical techniques can be conducted using any suitable technique given the context provided herein. In some implementations, it may be done using an optical measurement sensor that projects an optical beam having a first wavelength range that is selected so as to stimulate emission of light having a second wavelength range from the THC adduct. The emitted light may then be collected by the same optics used for projection and routed to a photodetector in the optical measurement sensor for quantification. A photoemitter may be located so as to direct light along a first axis and a photodetector may be configured to receive light received along a second axis that is orthogonal to the first axis. A beam splitter, e.g., a window that is generally reflective to the first wavelength range but generally transmissive to the second wavelength range, may be located at the intersection of the first axis and the second axis, and may be positioned at a 45° angle to both axes so as to cause light from the photoemitter to be turned 90° and directed out of the optical measurement sensor to form the optical beam. At the same time, light that is emitted by the THC adduct in response to stimulation by the light of the first wavelength range may pass through the beam splitter without being reflected and thus be received by the photodetector. When measurement of the amount of THC adduct present in a sample is desired, the photoemitter may be turned on so that light of the first wavelength range is emitted to optically pump or stimulate the THC adduct; the light of the second wavelength range that is emitted by the THC adduct in response may then be measured by the photodetector, and the intensity of such detected light may be correlated with an amount or concentration of THC adduct (and thus THC) that is present in the sample. It is to be understood that other types of optical sensors may be used as well, and that some optical sensors may, depending on the particular adduct used, not include a photoemitter, e.g., in implementations where the THC adduct does not require optical pumping in order to emit light. In various embodiments, data corresponding to the determined quantity of THC may be wirelessly transmitted from the detection location to a remote location by any suitable technique.

In various implementations, prior to the exposing the sample adduct to the light source, the fluorophore is activated. The fluorophore is activated by introducing charge into the sample adduct nonpolar phase. For example, charge may be introduced into the sample adduct nonpolar phase by routing the adduct nonpolar phase through a charge-donating conduit prior to exposure to the light source (e.g., acid-washed glass or uncoated hydrophobic polypropylene material (e.g., Repel Polymer Technology (RPT) pipette tip, available as TipOne from STARLAB GmbH or Hamburg, Germany), and/or applying a voltage to the sample adduct nonpolar phase, for example with a 9V battery. In other embodiments, charge may be introduced into the sample adduct nonpolar phase by adding acid to the mixture prior to solvent extraction to isolate the sample adduct in the nonpolar phase. For example, 1M HCl may be added to the mixture to introduce charge. In this way, a fluorophore-activated fluorescent-labeled THC-adduct, the adduct dissolved in a nonpolar adduct solution, is formed.

In various implementations, prior to detecting THC by the exposing the adduct to the light source, the adduct is separated from non-target molecular species and fluorescence strength of the fluorophore is improved by removing the nonpolar phase from contact with the polar phase following solvent extraction, for example with a siphon.

Detecting by determining an amount of THC in the captured breath sample based on the measured fluorescence of the isolated and activated fluorescent-labeled THC sample adduct can be accomplished by exposing the sample adduct in the nonpolar phase to a light source to produce a fluorescence, measuring the fluorescence, and determining a quantity of THC captured and collected from the breath sample based on the measured fluorescence of the sample adduct in the nonpolar phase. In various embodiments, determining the quantity of THC based on the measured fluorescence of the sample adduct in the nonpolar phase involves a comparing the fluorescence of the sample adduct in the non-polar phase to the fluorescence of one or more standard positive and/or negative controls. This can be accomplished by adding to one or more standard/control/calibration THC solutions containing a known amount of THC (including, in the case of a negative control, no THC), the basic buffer and the aqueous diazotized fluorophore solution to form one or more fluorescent-labeled THC standard adducts in standard adduct solutions. The standard adduct solutions are then processed in the same manner as the sample adduct solution, for example in each case adding to the standard adduct solution the nonpolar organic solvent and mixing, and separating the mixture into polar and nonpolar phase layers, wherein the nonpolar layer contains the fluorescent-labeled THC standard adduct, if any. In various embodiments, these standard (control or calibration) adduct solutions are prepared in parallel with the sample adduct solution, and using the same reagents to minimize variation. In particular, the sample and standard adduct solutions can be prepared using the same diazotized fluorophore solution added to each control THC solution, since it can be difficult to prepare diazotized fluorophore solutions consistently. Thereafter, the standard adduct solutions may be subjected to the same detection procedure as the sample adduct. Comparisons of the fluorescence measurements of the standards and the sample can facilitate more accurate determination of a quantity of THC captured and collected from a breath sample.

FIG. 3 depicts a schematic of an example target substance analysis system in conjunction with which the methods and compositions described and claimed herein may be implemented. Additional aspects of such a system are described in U.S. Provisional Application No. 62/351,821 filed Jun. 17, 2016, and titled "SYSTEM AND METHOD FOR TARGET SUBSTANCE IDENTIFICATION," and concurrently filed application Ser. No. 15/217,264 titled "SYSTEM AND METHOD FOR TARGET SUBSTANCE IDENTIFICATION," incorporated by reference herein for the purpose of describing an example operational context for the described methods and compositions.

In FIG. 3, the example target substance analysis system is configured to facilitate the detection of tetrahydrocannabinol (THC) in a person's breath, thereby allowing for portable breath testing unit (e.g., Breathalyzer)-type testing for people suspected of being under the influence of THC. As will be appreciated from the following discussion, the detection of THC in a breath sample may involve a number of different steps, and it is to be understood that while these steps are described with respect to a particular embodiment of a THC analysis system, other embodiments falling within the scope of this disclosure may operate differently from the specific examples discussed but may nonetheless still fall within the scope of the disclosure.

In FIG. 3, the analysis system 100 includes components grouped into three general assemblies: a cartridge 102, a base station 104, and a breath capture module 106. These three assemblies may be interconnected or disconnected during operation to facilitate the analysis of a captured breath constituent sample. It is to be understood that other implementations of the concepts discussed herein may offer similar capabilities, but without one or more of such assemblies (or using similar, but different, assemblies).

In the depicted implementation, components relating to the collection of a breath constituent sample from a subject may be contained in a breath capture module (BCM) 106. Such a BCM may be designed to be relatively lightweight and may have features, such as a catch media 114, that are configured to promote the capture of breath constituents from a person's breath as the person exhales through the BCM 106. The BCM 106 may also include a mouthpiece 108, to allow the person to exhale into the BCM 106, and a saliva trap 110, which may prevent or hinder saliva or spittle from reaching the catch media 114. The BCM may also include electronics (not shown), such as one or more processors and a memory storing instructions for controlling the one or more processors, that may control or monitor operation of the BCM 106 and provide information regarding the progress of the sample collection using the BCM 106. For example, the BCM 106 may include a pressure sensor 112 that has a pressure measurement port that is interposed between the saliva trap 110 and the catch media 114 so as to monitor the pressure downstream of the saliva trap 110 and upstream of the catch media 114. The one or more processors may monitor the data from the pressure sensor and determine therefrom the amount of air that is blown into the mouthpiece 108, through the saliva trap 110, and then delivered to the catch media 114. When the amount of exhaled breath that passes through the BCM 106 exceeds a predetermined amount (as determined from the pressure sensor data, or from another sensor providing similar information), e.g., 3 liters, then the one or more processors may cause a signal to be provided that a sufficient sample has been collected, e.g., the BCM 106 may be caused to emit a "beep" or provide some other sort of indication that a sufficient sample has been collected.

After a breath constituent sample is collected in the BCM 106, the BCM 106 may be connected to the cartridge 102 to allow the breath constituent sample to be drawn out of the BCM 106 and analyzed by the analysis system 100.

The cartridge 102 may include a number of reservoirs that contain various chemicals used in the target substance detection techniques used by the analysis system 100. These reservoirs may be configured to allow the fluids contained in each reservoir to be independently dispensed, as needed, during the analysis process. In some cases, one or more of the reservoirs may also be configured to allow fluids outside of the reservoirs to be drawn into the reservoir. In the depicted example analysis system 100, the reservoirs 120 take the form of syringes, each of which is actuated by a corresponding actuator 118. The actuators 118 may be located in the base station 104, which may be a larger unit that includes various "durable" systems or components, e.g., the actuators 118, an optical sensor 152, electronics (not shown), power supply components (not shown), etc. The cartridge, which may include various "consumable" elements, e.g., chemicals used during the analysis, may be removably insertable or connectable with the base station to allow for easy replacement of the consumable elements.

It is to be understood that while syringes and actuators are used in the depicted example system, other fluid storage and dispensing systems may be used in place of, or in addition to, such syringe-based systems. Such alternative implementations are to be understood as also being within the scope of this disclosure.

In the depicted example, each of the reservoirs 120 is connected to a common manifold 128 (which may, for example, be provided by two or more separate manifolds 130 and 132 that are linked together via a tube or other connection so as to form the common manifold 128; this was done to allow commercial off-the-shelf manifolds to be used, and could be avoided by custom-manufacturing a single, integrated manifold). Each such connection of a reservoir 120 to the manifold 128 may include a corresponding valve 122 that may be opened or closed to prevent fluid flow between the corresponding reservoir 120 and the manifold 128. In some instances, there may be an additional diverter or 3-way valve that is also interposed between some of the reservoirs 120 and the manifold 128 to allow the fluid that is stored in such reservoirs to be delivered not only to the manifold 128, but also alternatively to another location. In such scenarios, the functionality of the diverter valve and the shut-off valve may be combined into a single valve structure, e.g., a 3-way valve with an integral shut-off capability.

The common manifold may also be configured to allow fluids from the reservoirs 120 to be directed to one or more downstream components, such as a mixing chamber 136, a first activation cell 142, a second activation cell 144, an optical measurement chamber 146, a waste receptacle 148, or other downstream component.

EXAMPLES

The following examples provide workflow summaries of benchtop protocols for THC detection using solvent extraction in accordance with the present disclosure, that may be used or adapted for use in roadside detection and quantification of THC obtained from a breath sample taken using a handheld device. These examples are provided to exemplify and more clearly illustrate aspects of the present disclosure, and/or provide proof-of-concept, and are in no way intended to limit the scope of the coverage provided by this application to the specific details described.

Example 1

Materials
Glass vials for all reaction chemistries and to hold all buffers and intermediates
Glass pipettes for mixing and cleaning
P1000 pipettor
Scale (measurement accuracy and precision <0.1 mg)
1000 uL pipette tips (TipOne, RPT, USA Scientific) for metering
Solvents: ethanol, MTBE, heptane
Buffers/pH modifiers: acidic (100 uM HCl) and basic buffer (20 mM $NaHCO_3$ and 13 mM $Na_2CO_2$—pH 9.87)
Reagents: Mix C powder (rhodamine-123, camphorsulfonic acid (CSA), sodium nitrite mixture) (maintain dry, e.g., using desiccant, prior to use)
Prototype optical system with glass cuvette
Air or nitrogen cylinder for drying sample cuvette
Diazonium Reaction with THC Protocol: (Solvent Extraction Protocol Per Sample)
1. Pipette necessary ratio of THC:EtOH to reach a final volume of 250 uL
   a. Assay typically ranges from 0 to 2 ng THC
2. Add 500 uL of buffer solution (20 mM $NaHCO_3$ and 13 mM $Na_2CO_3$)-pH 9.87
3. In separate vial, measure 1.0 mg rhodamine, CSA, sodium nitrite mixture.
4. In a separate vial, prepare 1 mL of 75:25 Heptane:MTBE
5. Add 250 uL of 100 uM HCl to rhodamine, camphorsulfonic acid (CSA), sodium nitrite mixture powder. Allow to stand for 100 seconds.
6. Add 250 uL of rhodamine, camphorsulfonic acid (CSA), sodium nitrite mixture solution to THC:EtOH solution
7. Add 1 mL of 75:25 Heptane:MTBE solution.
8. Using a glass Pasteur pipette, pipette mixture up and down for 30 seconds
9. Separation: Carefully pipette 650 uL from top layer of solution; DO NOT TAKE ANY OF THE BOTTOM LIQUID.
10. Activation is achieved by using RTP pipette tips.
11. Detection: Analyze on optical system.
Note: Assume 3 mL of ethanol total for rinsing optical flow cell between each measurement.
Optical System Procedure:
1. Turn on Arduino and run LED for one hour prior to any testing
2. Measure 5 boluses (500 uL each bolus) of 100% ethanol to ensure a stable baseline
   a. Make sure temperature reading falls below 45° C. before capturing
   b. Capture data using Hyper Terminal for 15 seconds for each bolus
3. Record optical signal (V) displayed on LCD screen 4. Remove as much ethanol as possible using a glass Pasteur pipette and dry cuvette with compressed air for 10 seconds
5. Input 500 uL of sample into cuvette and immediately capture data for 15 seconds
6. Record optical signal (V) displayed on LCD screen
7. Remove as much of the sample as possible using a glass Pasteur pipette
8. Input 1 mL of ethanol into cuvette and pipette up and down using a glass Pasteur pipette 10 times
9. Remove ethanol and repeat step 8
10. Input 500 uL of 100% ethanol into cuvette and capture data for 15 sec
    a. Make sure detector temperature reading falls below 45° C. before capturing
11. Repeat steps 4-10 for each sample to be tested Example 2

Solvents: DI water, EtOH, MTBE, Heptane
Reagents: Mix C powder (rhodamine, CSA, sodium nitrite mixture)
Buffers and pH modifiers: acid (100 uM HCl) and basic buffer (20 mM NaHCO3 and 13 mM Na2CO3 @pH 9.87)
Basic Buffer Stock
    1. Add 0.84 g $NaHCO_3$ (sodium bicarbonate) and 0.67 g Na2CO3 (sodium carbonate) to 500 mL DI water
    2. Shake manually (about 3-5 minutes) and visually confirm that all granules have gone into solution
    3. Use pH meter to check pH (should be around 9.87)
    4. Final concentrations: 1.68 g/L (20 mM) $NaHCO_3$ and 1.34 g/L (13 mM) Na2CO3
Making Mix C Powder
  Basic Mass Ratios
    1. 1.35 mg rhodamine-123
    2. 0.867 mg 10-CSA (camphorsulfonic acid)
    3. 200 mg NaNO2 (sodium nitrite)
  Process
    1. Clean mortar and pestle (finishing with EtOH) and dry completely
    2. Weigh out rhodamine-123 first
    3. Add other components in above mass ratios
    4. Grind powder with mortar & pestle for about 1.5 minutes, scraping the surfaces with a small scoop every 30 seconds
    5. Store Mix C powder in light-tight glass vial inside desiccator
Heptane/MTBE Solvent
    1. Mix in 75/25 v/v heptane/MTBE ratio to create organic solvent
Making Diazonium
    1. For each sample, weigh out 1 mg Mix C (single vial for all samples, including controls, simultaneously)
    2. When ready for assay, add 250 uL 100 uM HCl for each sample (single vial for all samples simultaneously) and wait 2.5 minutes before adding to each sample
Nominal Assay Volumes
    1. THC positive control, negative control, and THC sample all in 250 uL EtOH
    2. Add 500 uL Basic Buffer added to each sample and mix
    3. Add 250 uL diazonium solution and mix
    4. Add 1 mL Heptane/MTBE solvent to existing 1 mL sample and mix
Separation
Activation
Detection: Optical Measurement It is to be understood that the above-described methods may be implemented in a number of different ways, and that such different implementations are also considered within the scope of this disclosure.

What is claimed is:

1. A method of detecting THC in exhaled breath, comprising:
    combining THC captured from an exhaled breath sample with a diazotized fluorophore in a solution to form a fluorescent-labeled THC adduct;
    detecting and determining a quantity of the THC captured from the exhaled breath sample by exposing the fluorescent-labeled THC adduct to a light source to produce a fluorescence and measuring the fluorescence.

2. The method of claim 1, wherein the diazotized fluorophore is a xanthene.

3. The method of claim 2, wherein the xanthene is a rhodamine.

4. The method of claim 3, wherein the rhodamine is Rhodamine-123.

5. The method of claim 1, wherein the fluorescent-labeled THC adduct is a composition of formula:

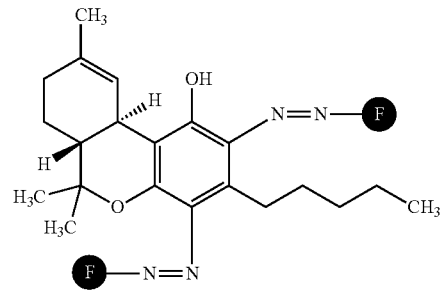

wherein:
    F is the fluorophore,
    and the —N═N—F group is present at the para and/or ortho positions of the THC phenol ring.

6. The method of claim 5, wherein only one or the other —N═N—F group is present.

7. The method of claim 6, wherein the F—N═N— group is present only at the para position.

8. The method of claim 6, wherein the F—N═N— group is present only at the ortho position.

* * * * *